United States Patent
Mainella

(10) Patent No.: US 11,273,122 B2
(45) Date of Patent: *Mar. 15, 2022

(54) COMBINATION OF CANNABIS, DERIVATIVES THEREOF AND ADDITIVES IN ORAL CARE COMPOSITIONS

(71) Applicant: Therese Mainella, Northport, NY (US)

(72) Inventor: Therese Mainella, Northport, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/787,215

(22) Filed: Feb. 11, 2020

(65) Prior Publication Data

US 2021/0244653 A1    Aug. 12, 2021

(51) Int. Cl.

| | |
|---|---|
| *A61K 31/352* | (2006.01) |
| *A61Q 11/00* | (2006.01) |
| *A61K 8/98* | (2006.01) |
| *A61K 35/644* | (2015.01) |
| *A61K 31/59* | (2006.01) |
| *A61K 35/02* | (2015.01) |
| *A61K 8/42* | (2006.01) |
| *A61K 8/22* | (2006.01) |
| *A61K 8/24* | (2006.01) |
| *A61K 8/34* | (2006.01) |
| *A61K 8/49* | (2006.01) |
| *A61K 8/67* | (2006.01) |
| *A61K 8/35* | (2006.01) |
| *A61K 8/60* | (2006.01) |
| *A61K 8/63* | (2006.01) |
| *A61K 33/40* | (2006.01) |
| *A61K 33/10* | (2006.01) |
| *A61K 33/42* | (2006.01) |
| *A61K 31/17* | (2006.01) |
| *A61K 31/05* | (2006.01) |
| *A61K 31/375* | (2006.01) |
| *A61K 31/122* | (2006.01) |
| *A61K 31/714* | (2006.01) |
| *A61K 31/355* | (2006.01) |

(52) U.S. Cl.
CPC ............. *A61K 8/988* (2013.01); *A61K 8/22* (2013.01); *A61K 8/24* (2013.01); *A61K 8/347* (2013.01); *A61K 8/355* (2013.01); *A61K 8/42* (2013.01); *A61K 8/498* (2013.01); *A61K 8/60* (2013.01); *A61K 8/63* (2013.01); *A61K 8/676* (2013.01); *A61K 8/678* (2013.01); *A61K 31/05* (2013.01); *A61K 31/122* (2013.01); *A61K 31/17* (2013.01); *A61K 31/355* (2013.01); *A61K 31/375* (2013.01); *A61K 31/59* (2013.01); *A61K 31/714* (2013.01); *A61K 33/10* (2013.01); *A61K 33/40* (2013.01); *A61K 33/42* (2013.01); *A61K 35/02* (2013.01); *A61K 35/644* (2013.01)

(58) Field of Classification Search
CPC ............................. A61K 8/988; A61K 31/352
See application file for complete search history.

(56) References Cited

U.S. PATENT DOCUMENTS

| | | | |
|---|---|---|---|
| 4,454,374 A | 6/1984 | Pollack | |
| 6,419,905 B1* | 7/2002 | Alvarez Hernandez | A61K 8/19 424/49 |
| 10,285,916 B2 | 5/2019 | Sagel et al. | |
| 2002/0037258 A1* | 3/2002 | Dodd | A61K 6/69 424/49 |
| 2016/0166498 A1* | 6/2016 | Anastassov | A61K 8/463 424/52 |
| 2016/0279077 A1* | 9/2016 | De Vries | A61K 9/2018 |
| 2018/0078523 A1 | 3/2018 | Shmulewitz et al. | |
| 2018/0125980 A1* | 5/2018 | Finley | A61K 31/045 |
| 2019/0076349 A1 | 3/2019 | Anastassov et al. | |
| 2020/0000765 A1* | 1/2020 | Borok | A61Q 19/00 |
| 2021/0212983 A1* | 7/2021 | Greenbaum | A61K 47/10 |

FOREIGN PATENT DOCUMENTS

WO    2019155337    8/2019

OTHER PUBLICATIONS

PA Nayak, UA Nayak, and R. Mythili. "Effect of Manuka honey, chlorhexidine gluconate and xylitol on the clinical levels of dental plaque." Obtained from https://www.ncbi.nlm.nih.gov/pmc/articles/PMC3220139/?report=printable on Apr. 2, 2020, originally published 2010, 8 printed pages. (Year: 2010).*

SP Mangaiyarkarasi, T Manigandan, M Elumalai, PK. Cholan, Roopam Pal Kaur. "Benefits of Aloe Vera in Dentistry." Obtained from https://www.ncbi.nlm.nih.gov/pmc/articles/PMC4439686/?report=printable on Apr. 2, 2020, originally published 2015, 9 printed pages. (Year: 2015).*

José M. Alvarez-Suarez, Massimiliano Gasparrini, Tamara Y. Forbes-Hernández, Luca Mazzoni, and Francesca Giampieri. "The Composition and Biological Activity of Honey: A Focus on Manuka Honey." Foods, vol. 3, 2014, pp. 420-432. (Year: 2014).*

Helen K P English, Angela R C Pack, and Peter C Molan. "The effects of manuka honey on plaque andgingivitis: a pilot study.—Pubmed Abstract." https://pubmed.ncbi.nlm.nih.gov/15125017/ accessed Apr. 1, 2021, originally published Apr. 2004, 1 printed page. (Year: 2004).*

Cannuka. https://web.archive.org/web/20180301011948/https://cannuka.com/accessed Dec. 27, 2021, originally published Mar. 1, 2018 based upon the Internet Archive Wayback Machine, pp. 1-5. (Year: 2018).*

Sharma, et al. C-Lobe of Lactoferrin: The Whole Story of the Half-Molecule, Biochemistry Research International vol. 2013, Article ID 271641, 8 pages.

\* cited by examiner

*Primary Examiner* — Isaac Shomer

(74) *Attorney, Agent, or Firm* — Porzio Bromberg & Newman P.C.

(57) ABSTRACT

The present invention relation to an oral care composition comprising a cannabinoid and at least one pharmaceutical active component is provided in which the at least one pharmaceutical active component improves oral health beyond benefits provided by the at least one cannabinoid alone. The at least one pharmaceutical active component can be Manuka honey. The oral care composition can be used in an oral care product for whitening or bleaching teeth.

11 Claims, No Drawings

COMBINATION OF CANNABIS, DERIVATIVES THEREOF AND ADDITIVES IN ORAL CARE COMPOSITIONS

BACKGROUND OF THE INVENTION

Field of the Invention

The present invention relates to oral care compositions including materials derived from the *cannabis* plant and additives to improve health of the oral environment. The oral care compositions can be used, for example, in toothpaste, interdental devices, custom trays, mouthwash, mouth rinse, tooth powder, tooth gel, tooth mousse, tongue gel, lozenges and/or whitening gel or strips to place the oral care composition directly on tooth surfaces.

Description of Related Art

Cannabinoid oral care compositions have been described. US Patent Application Publication No. US 2019/0076349 describes cannabinoid oral care compositions which can be used in dentifrice in paste and powder form and mouthwash. In the composition, at least one cannabinoid is present in an amount adequate to give anti-bacterial properties to the dentifrice; while at the same time is unlikely to cause an overdose of anti-bacterial compounds.

Pharmaceutical combinations of cannabinoids and other agents capable of increasing the potency, decreasing the therapeutic dosages, reducing the side-effects and/or prolonging the therapeutic window of cannabinoids have been described in US Patent Application Publication No. US 2018/0078523. This US Patent Application Publication describes beneficial combinations of cannabinoids and N-acylethanolamines.

WO 2019/155337 describes the combination of plant extract and at least one cannabinoid results in a therapeutic effect selected from a synergistic effect, an additive effect, a potentiating effect and any combination thereof.

It is desirable to provide an improved oral care composition including a combination of an active component of a *cannabis* material with a specified pharmaceutical active ingredient or combination of active ingredients to provide additional benefits in improving oral health beyond the benefits provided by the *cannabis* related material alone.

SUMMARY OF THE INVENTION

According to an aspect of the present invention there is provided an oral care composition comprising a therapeutically-effective amount of at least one cannabinoid and at least one pharmaceutical active component in which the at least one pharmaceutical active component improves oral health beyond benefits provided by the at least one cannabinoid alone.

Optionally, the at least one pharmaceutical active component is Manuka honey. Optionally, the pharmaceutical active component can include one or more whitening ingredients. Optionally, the pharmaceutical active component can include an abrasive. Optionally, the pharmaceutical active component can include one or more desensitizing agents. Optionally, the pharmaceutical active component can include one or more vitamins, minerals, extracts, tocopherols, herbs and spices.

Optionally, the cannabinoid is selected from cannabidiol (CBD), cannabigerol (CBG) and cannabichromene (CBC), and Cannabidiphorol (CBDP).

Optionally the oral care composition further comprises an orally acceptable carrier. Optionally the orally acceptable carrier is an orally acceptable carrier for toothpastes, interdental devices, custom trays, mouthwashes, mouth rinses, tooth powders, tooth gels, tooth mousses, tongue gels, lozenges, whitening gels or whitening strips.

Optionally the oral care composition can comprise one or more additives selected from diluents, preservatives, humectants, sweeteners, thickeners, flavorings, emulsifiers, emollients, surfactants, and mixtures thereof.

Optionally, the oral care composition is for teeth whitening or bleaching. Oral care products comprising the oral care composition can have various modes of delivery including syringes, tubes, dual barrel syringes, jars, cartridges, custom trays, strips and the like for delivering the oral care composition.

The present invention is also directed to methods to prepare an oral care product and methods to administer the oral care product to a human subject.

DETAILED DESCRIPTION

It will be readily understood that the components of the present invention, as generally described herein, could be arranged and designed in a wide variety of different configurations or formulations. Thus, the following more detailed description of the embodiments of the system, products and methods of use of the present invention, are not intended to limit the scope of the invention, as claimed, but is merely representative of various embodiments of the invention.

In one embodiment, an oral care composition can include a therapeutically-effective amount of at least one cannabinoid and at least one pharmaceutical component as an active component. A pharmaceutical active component can be comprised of any suitable materials. Generally, a pharmaceutical active component provides additional benefits to help improve and/or maintain oral health above and beyond the basic benefits provided by a cannabinoid. Any number of compounds or materials can be utilized to comprise a pharmaceutical active component of an oral care product.

Cannabinoids used in the oral care composition can be in liquid form, as a natural constituent of hemp oil or *cannabis* oil. Hemp oil or *cannabis* oil is harvested by cold pressing the seeds and the plants of the *Cannabis sativa* species, as described in US Patent Application Publication No. 2019/0076349, hereby incorporated by reference into this application. The resulting oil is extracted using $CO_2$ extraction or solvent extraction process and can be further concentrated by distillation. Targeted cannabinoids include cannabidiol (CBD), cannabigerol (CBG) and cannabichromene (CBC) and Cannabidiphorol (CBDP).

Suitable compounds or materials in a pharmaceutical active component can include an anti-bacterial or anti-microbial component. In one embodiment, the pharmaceutical active component is an anti-microbial honey. The anti-microbial honey can be Manuka honey which is a type of honey native to New Zealand. Manuka honey is produced by bees who pollinate the flower *Leptospermum scoparium*, commonly known as the Manuka bush. Manuka honey features antibacterial properties. Methylglyoxal is an active ingredient in Manuka honey and is likely responsible for the antibacterial effects. Manuka honey, without limitation, has antiviral, anti-inflammatory, antioxidant benefits, wound healing and preventative therapy properties.

In one embodiment, the pharmaceutical active component can include one or more whitening ingredients. Suitable compounds or materials for whitening ingredients can include, without limitation, carbamide peroxide, hydrogen peroxide, sodium perborate and calcium peroxide. This embodiment is useful in custom trays, whitening gel or strips, toothpastes and the like.

In one embodiment, the pharmaceutical active component can include an abrasive. Suitable compounds or materials for abrasives can include, without limitation, calcium carbonate, bicarbonate, diatomaceous earth, kaolin, hydroxyapatite, phosphorus, bio-active glasses, and the like. This embodiment is useful in toothpaste, tooth powder, tooth gel, tooth mousse, and tongue gel.

In one embodiment, the pharmaceutical active component can include one or more desensitizing agents. Suitable compounds or materials for desensitizing agents, without limitation, can include potassium nitrate and sodium fluoride or the like.

In one embodiment, the pharmaceutical active component can include one or more vitamins or minerals. Vitamins can include, for example, vitamin C, D, K, B12. Vitamin D and K can have a biological role is to help move calcium into the proper areas in your body, including bones and teeth. B12-methyl cobalamin and cyanocobalamin can be used as a source for B12. In one embodiment, the pharmaceutical active component can include one or more tocopherols including, without limitation, Vitamin E and similar vitamins. Minerals can include for example calcium, potassium and phosphorous.

In one embodiment, the pharmaceutical active component can include one or more extracts, herbs and spices to supplement or improve health properties of an oral care product. For example, the extracts can include vegetable and fruit extracts, as well as stem cells of plants. The additives can include adaptogenic herbs including, without limitation, strawberry, aloe vera, kakadu plum, licorice root, *eucalyptus* stem cells, and the like.

In some embodiments, the composition can comprise one or more additives to provide desired properties of an oral care product. In one embodiment, the additives can include preservatives, without limitation, including sodium benzoate and the like. In one embodiment, the additives can include humectants including, without limitation, propylene glycol, vegetable glycerin, sorbitol and the like. In one embodiment, the additives can include thickeners including, without limitation, xanthan gum, candelilla vegan wax, bees wax, wax, magnesium stearate, agar, and the like.

In one embodiment, an adhesive composition can include an aqueous gelling agent. Suitable gelling agents include carboxypolymethylene, carboxymethyl cellulose, carboxypropyl cellulose, polyoxamers, carrageenan, Veegum, carboxyvinyl polymers, and natural gums such as gum karaya, xanthan gum, Guar gum, gum arabic, gum tragacanth, and mixtures thereof.

In still a further embodiment, the oral care composition can include emulsifiers as an additive. Suitable emulsifiers include PEG-free non-ionic oil-in-water emulsifier, for example as manufactured by Lotioncrafter as OLIVEM 1000.

In still a further embodiment, the oral care composition can include surfactants as an additive. Any orally acceptable surfactant, most of which are anionic, nonionic or amphoteric, can be used. Suitable surfactants can include propylene glycol, decyl glucoside, sodium cocoyl glutamate, coco glucoside and the like.

In still a further embodiment, the oral care composition can include clay as an additive.

In a still further embodiment, the oral care composition of the invention can comprise at least one colorant as an additive. Any orally acceptable colorant can be used. Colorants herein include pigments, dyes and agents. In one embodiment, the colorants impart a particular luster or reflectivity to teeth. Suitable pigments can include Hybiscus Pitaya, Butterfly Pea and the like.

In a still further embodiment, the oral care composition can comprise at least one emollient as an additive. Any orally acceptable emollient can be used. Suitable emollients can include avocado Oil, CBD oil, CBG oil, CBDP oil and the like.

In one embodiment, the additives can include sweeteners to provide desired product taste characteristics of the oral care product. Suitable sweeteners can include xylitol, sorbitol, stevia, honey, fruit extract and the like.

In one embodiment, the additives can include flavorings to provide desired product taste characteristics of the oral care product. Suitable flavorings include natural and artificial flavorings.

Water is a preferred diluent and in some compositions such as mouthwashes, water is commonly accompanied by an alcohol, e.g., ethanol.

The composition can comprise from about 0.1% to about 60% by weight or by volume of the cannabinoid, for example, 1.0-50%, 5-45%, 10-40%, 20-40%, 25-40%, or 30-40% by weight or by volume.

The composition can comprise from about 0.1% to about 45% by weight or by volume of the pharmaceutical or otherwise active agent, for example, 0.1-1.0%, 0.1-0.9%, 0.1-0.8%, 0.1-0.7%, 0.1-0.6%, 0.1-0.5%, 0.1-0.3%, 0.1-0.2%, 1%-45%, 5%-40%, 10-35%, 10-30%, 15-30.%, 20-30% or 25-30% by weight or by volume. In one embodiment the pharmaceutical or otherwise active agent is Manuka honey which is present in an amount of 1 to 40%, 1 to 30%, 5-40%, 10-35%, 10-30%, 15-30.%, 20-30% or 25-30% by weight or by volume.

The composition can comprise from about 0.1% to about 10% by weight or by volume of the additive, for example, 0.1-1.0%, 0.1-0.9%, 0.1-0.8%, 0.1-0.7%, 0.1-0.6%, 0.1-0.5%, 0.1-0.3%, 0.1-0.2%, 1-5%, 2-5%, 2-6%, 3-8%, 4.0-9%, 5-8%, 6-9%, 5-10%, 7-10%, or 9-10%, by weight or by volume.

The composition can comprise from about 0.1% to about 60% by weight or by volume of one or more whitening ingredients, for example 1-60%, 1-50%, 5-50%, 5-45%, 5-40%, 10-35%, 15-30.%, 20-30% or 25-30% by weight or by volume.

In one embodiment, the composition comprises a cannabinoid present in an amount of about 1% to about 30% weight percent of the composition, Manuka honey present in an amount of about 1% to about 20% weight percent of the composition and a whitening ingredient present in an amount of about 1% to about 50% weight percent of the composition.

The cannabinoid and pharmaceutical according to the present invention can include pharmaceutically acceptable forms thereof, including isomers such as diastereomers and enantiomers, salts, solvates, and polymorphs, as well as racemic mixtures.

The composition can be formulated by mixing two or more of the ingredients at room temperature. In one embodiment, all ingredients of the composition can be mixed at room temperature. Alternatively, the ingredients during mixing are heated from about 50° C. to 100° C., from about 50° C. to 95° C., 50° C. to 85° C. 50 or from about 50° C. to 100° C.

Delivery

The oral care composition of the present invention preferably comprises an orally acceptable carrier for use in a product such as a toothpaste, interdental device, mouthwash, mouth rinse, tooth powder, tooth gel, tooth mousse, tongue gel, lozenges and/or whitening gel or strips, formulations to be delivered through devices such as pens, back of a toothbrush and front of a toothbrush, formulations to be delivered through porous wicking materials, interdental brushes, fluid encased dental strips, floss impregnated or coated with the formulations or dried formulations, portables, oral trays peelable gels, and patches. Other modes of delivery include custom trays, syringes, tubes, dual barrel syringes, jars, and cartridges. Accordingly, opportunities exist for professional use of the compositions of the present invention for example during cleanings routine prophylaxis treatments, irrigations, or aggressive periodontal procedures, such as root planning & scaling, whitenings and restorative procedures). The composition of the invention may be provided in any of the products defined herein. If used in animals or pets, veterinary pastes, chewables or treats may also be used as the orally acceptable carrier.

Methods of Use

The oral care composition according to the present invention can be administered to or applied to a human or other animal subject. The oral care composition may be suitable for administration or application to the oral cavity of a human or animal subject. In one embodiment, the oral care composition is for whitening teeth, removal of and control of formation of biofilm, and/or removing tooth stains. Reduces inflammation and reduce plaque formation. The oral care composition can also reduce the formation of plaque and biofilm. Furthermore, the reduction or removal of plaque can occur through an inhibition of biofilm (a plaque precursor) formation and/or degradation of microbial biofilm. The present invention provides a method of whitening teeth and improving oral health in a subject comprising administering a therapeutically effective amount of a composition comprising a therapeutically-effective amount of at least one cannabinoid and at least one pharmaceutical active component. Preferably, the composition is an oral care composition as defined herein, and the composition is applied to the oral cavity.

The present invention further provides a use of comprising a therapeutically-effective amount of at least one cannabinoid and at least one pharmaceutical active component, wherein the at least one pharmaceutical active component improves oral health beyond benefits provided by the at least one cannabinoid alone, in an oral care composition, for whitening teeth in the oral cavity of a subject. The oral care composition is preferably as defined herein.

The invention is further illustrated in the following non-limiting examples. The examples are given solely for the purposes of illustration and are not to be construed as limitations of the present disclosure.

Example 1

An example composition with ingredient ranges for a whitening toothpaste can be formulated as shown in Table 1.

TABLE 1

| INGREDIENT | % w/w |
| --- | --- |
| Water | 25.000 |
| Sodium Benzoate | 3.000 |

TABLE 1-continued

| INGREDIENT | % w/w |
| --- | --- |
| Vegetable Glycerin | 10.000 |
| Xanthan gum | 0.800 |
| Xylitol | 8.000 |
| Sorbitol | 9.000 |
| Fruit Extract | 0.100 |
| Wax | 1.000 |
| Magnesium Stearate | 1.500 |
| Emulsifier | 5.000 |
| Vegetable Extract | 1.500 |
| CBD oil | 1.250 |
| CBG oil | 1.250 |
| Flavor | 1.050 |
| Vitamins/Minerals | 0.050 |
| Calcium Carbonate | 12.000 |
| Bicarbonate | 2.500 |
| Clay | 4.000 |
| Decyl Glucoside | 3.000 |
| Manuka Honey | 10.00 |
| TOTAL | 100.000 |

The ingredients are mixed. Water and sodium benzoate are stirred and heated to 75° C. in phase A. Xanthan gum, glycerin and Manuka honey are stirred and heated to 75° C. in phase B. Phase A is added to phase B. Sorbitol, xylitol, fruit extract and Aloe Vera are combined to the mixture of phase A and phase B to form phase C. Phase D ingredients of waxes, magnesium stearate, emulsifier, avocado oil and CBD/CBG oils are mixed and heated to 75° C. Phase C was added to Phase D with stirring to form an oil in water emulsion. Once the temperature is below 50° C. vitamins and minerals are added. Calcium carbonate, bicarbonate, clay and decyl glucoside are added at room temperature.

Example 2

An example composition with ingredient ranges for a whitening toothpaste can be formulated as shown in Table 2.

TABLE 2

| INGREDIENT | % w/w |
| --- | --- |
| Water | 25.000 |
| Sodium Benzoate | 3.000 |
| Vegetable Glycerin | 10.000 |
| Xanthan gum | 0.800 |
| Xylitol | 8.000 |
| Sorbitol | 9.000 |
| Fruit Extract | 0.100 |
| Wax | 1.000 |
| Magnesium Stearate | 1.500 |
| Emulsifier | 5.000 |
| Vegetable Extract | 1.500 |
| CBD oil | 0.833 |
| CBG oil | 0.833 |
| CBDP | 0.833 |
| Flavor | 1.050 |
| Vitamins/Minerals | 0.050 |
| Calcium Carbonate | 12.000 |
| Bicarbonate | 2.500 |
| Clay | 4.000 |
| Decyl Glucoside | 3.000 |
| Manuka Honey | 10.00 |
| TOTAL | 100.000 |

The ingredients are mixed. Water and sodium benzoate are stirred and heated to 75° C. in phase A. Xanthan gum, glycerin and Manuka honey are stirred and heated to 75° C. in phase B. Phase A is added to phase B. Sorbitol, xylitol, fruit extract and Aloe Vera are combined to the mixture of phase A and phase B to form phase C. Phase D ingredients of waxes, magnesium stearate, emulsifier, avocado oil and CBD/CBG oils and CBDP are mixed and heated to 75° C. Phase C was added to Phase D with stirring to form an oil in water emulsion. Once the temperature is below 50° C. vitamins and minerals are added. Calcium carbonate, bicarbonate, clay and decyl glucoside are added at room temperature.

Example 3

An example composition with ingredient ranges for a whitening composition can be formulated as shown in Table 3.

Whitening Composition

TABLE 3

| INGREDIENTS | % w/w | % w/w | % w/w |
|---|---|---|---|
| Glycerin | 5.000 | 10.000 | 10.000 |
| Water | 40.000 | 55.000 | 40.000 |
| Hydrogen Peroxide 35% | 16.000 | 0.000 | 18.000 |
| Carboxypolymethylene | 5.000 | 4.900 | 3.000 |
| Sodium Hydroxide | 2.500 | 2.000 | 2.000 |
| Stevia/sweetener | 0.010 | 0.100 | 0.150 |
| Carbamide Peroxide | 10.000 | 20.000 | 0.000 |
| Propylene Glycol | 5.000 | 1.000 | 2.000 |
| CBD/CBG oil | 16.490 | 7.000 | 10.000 |
| Calcium | 0.000 | 0.000 | 14.850 |
|  | 100.000 | 100.000 | 100.000 |

The whitening composition can be prepared by mixing the ingredients. Compositions can be mixed at temperatures ranging from approximately room temperature 21° C. to 100° C.

It is to be understood that the above described embodiments are illustrative of only a few of the many possible specific embodiments, which can represent applications of the principles of the invention. Numerous and varied other arrangements can be readily devised in accordance with these principles by those skilled in the art without departing from the scope of the invention.

What is claimed is:

1. An oral care toothpaste composition comprising an orally acceptable carrier, a therapeutically-effective amount of at least one cannabinoid and at least one pharmaceutical active component, the at least one pharmaceutical active component comprises Manuka honey, the at least one cannabinoid is cannabidiol (CBD) and cannabigerol (CBG), the composition comprises from 1% to about 30% by weight or by volume of the at least one cannabinoid and about 0.1% to about 10.0% of the Manuka honey, wherein the toothpaste composition has antibacterial, anti-inflammatory, antioxidant, and wound healing properties.

2. The oral care composition of claim 1 wherein the at least one pharmaceutical active component further comprises an abrasive selected from the group consisting of calcium carbonate, bicarbonate, diatomaceous earth, kaolin, hydroxyapatite, phosphorus and bio-active glass.

3. The oral care composition of claim 1 wherein the at least one pharmaceutical active component further comprises a desensitizing agent.

4. The oral care composition of claim 1 wherein the at least one pharmaceutical active component further comprises a vitamin or mineral.

5. The oral care composition of claim 4 wherein the vitamin is selected from the group consisting of vitamin C, vitamin D, vitamin K, and vitamin B12.

6. The oral care composition of claim 1 wherein the at least one pharmaceutical active component further comprises a tocopherol.

7. The oral care composition of claim 1 wherein the at least one pharmaceutical active component further comprises one or more of extracts, herbs or spices.

8. The oral care composition of claim 1 wherein the at least one pharmaceutical active component further comprises one or more of strawberry, aloe vera, kakadu plum, licorice root or *eucalyptus* stem cells.

9. The oral care composition of claim 1 further comprising Cannabidiphorol (CBDP) and/or cannabichromene (CBC).

10. The oral care composition of claim 1 wherein the cannabinoid is in liquid or solid form.

11. The oral care composition of claim 1 wherein the composition further comprises one or more additives selected from diluents, preservatives, surfactants, thickening agents, emulsifiers, humectants, sweeteners, flavorants, pigments, emollients, and mixtures thereof.

* * * * *